(12) United States Patent
Sabelle et al.

(10) Patent No.: US 7,429,278 B2
(45) Date of Patent: Sep. 30, 2008

(54) N-ALKYLEHETEROARYL SECONDARY PARA-PHENYLENEDIAMINE AND COMPOSITION COMPRISING SUCH A PARA-PHENYLENEDIAMINE

(75) Inventors: Stéphane Sabelle, Paris (FR); Eric Metais, St-leu-le-Foret (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 11/863,316

(22) Filed: Sep. 28, 2007

(65) Prior Publication Data

US 2008/0069789 A1 Mar. 20, 2008

Related U.S. Application Data

(63) Continuation of application No. 11/066,455, filed on Feb. 28, 2005, now abandoned.

(60) Provisional application No. 60/568,263, filed on May 6, 2004.

(30) Foreign Application Priority Data

Feb. 27, 2004 (FR) .................................. 04 02024

(51) Int. Cl.
*A61Q 5/10* (2006.01)
*C07D 237/00* (2006.01)
*C07D 277/04* (2006.01)
*C07D 211/02* (2006.01)

(52) U.S. Cl. .................. 8/405; 8/406; 8/407; 8/408; 8/410; 8/412; 8/416; 8/424; 8/568; 8/573; 8/575; 544/224; 548/146; 546/249

(58) Field of Classification Search .............. 8/405, 8/406, 407, 408, 410, 412, 416, 424, 568, 8/573, 575; 544/224; 548/146; 546/249
See application file for complete search history.

(56) References Cited

U.S. PATENT DOCUMENTS

| | | |
|---|---|---|
| RE30,199 E | 1/1980 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 6,284,003 B1 | 9/2001 | Rose et al. |
| 6,530,960 B1 | 3/2003 | Pastore et al. |
| 6,645,258 B2 | 11/2003 | Vidal et al. |
| 6,730,789 B1 | 5/2004 | Birault et al. |
| 2003/0167579 A1 | 9/2003 | Lang |
| 2004/0255402 A1 | 12/2004 | Knuebel et al. |

FOREIGN PATENT DOCUMENTS

| | | |
|---|---|---|
| DE | 2359 399 A1 | 6/1975 |
| DE | 29 34 331 A1 | 3/1981 |
| DE | 3843 892 A1 | 6/1990 |
| DE | 4133 957 A1 | 4/1993 |
| DE | 195 43 988 A1 | 5/1997 |
| EP | 0 714 954 B1 | 6/1996 |
| EP | 0 770 375 B1 | 5/1997 |
| EP | 1 093 792 A1 | 4/2001 |
| FR | 2 586 913 A1 | 9/1987 |
| FR | 2 733 749 A1 | 11/1996 |
| FR | 2 801 308 A1 | 5/2001 |
| GB | 1026978 | 4/1966 |
| GB | 1153196 | 5/1969 |
| JP | 63-169571 A | 1/1990 |
| WO | WO 94/08969 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WP 94/08970 A1 | 4/1999 |
| WO | WO 01/66070 A1 | 9/2001 |
| WO | WO 02/28835 A1 * | 4/2002 |
| WO | WO 03/037875 A1 | 5/2003 |

OTHER PUBLICATIONS

STIC Search Report (U.S. Appl. No. 11/066,455) dated Mar. 12, 2007.*
S. Massa et al., Spiro-[4H-Pyrrolo[1,2-a][1,4]Benzodiazepine-4,4'-Piperidine] Derivatives As Potential Nootropic Agents: A Simple One-Pot Synthesis, 20 *Synthetic Communications*, 3537-3545 (1990).
Kotsuki et al., High Pressure Organic Chemistry; XII. A Convenient Synthesis of Aromatic Amines From Activated Aromatic Fluorides, 12 *Synthesis*, No., 1147-1148 (1990).
A copy of French Search Report, Oct. 2004.

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present disclosure is directed to a family of N-alkylheteroaryl secondary para-phenylenediamines, to their preparation, and to a cosmetic composition for dyeing keratin fibers, for example, human keratin fibers such as the hair, comprising, in a suitable dyeing medium, at least one N-alkylheteroaryl secondary para-phenylenediamine. Further disclosed herein is a process of dyeing keratin fibers, a ready-to-use composition, and a kit comprising at least two compartments.

28 Claims, No Drawings

N-ALKYLEHETEROARYL SECONDARY PARA-PHENYLENEDIAMINE AND COMPOSITION COMPRISING SUCH A PARA-PHENYLENEDIAMINE

CROSS-REFERENCE TO RELATED APPLICATIONS

This is a continuation of application Ser. No.11/066,455, filed Feb. 28, 2005 now abandoned, which claims the benefit of priority of French Patent Application No. 0402024, filed Feb. 27, 2004, and which also claims the benefit of priority of U.S. Provisional Application No. 60/568,263, filed May 6, 2004, all of which are incorporated herein by reference.

FIELD OF THE INVENTION.

The present disclosure relates to a novel family of N-alkylheteroaryl secondary para-phenylenediamines, to their preparation, and to their use in the oxidation dyeing of the hair.

BACKGROUND OF THE INVENTION

It is known practice to dye keratin fibers, and for example, human hair, with dye compositions comprising oxidation dye precursors, such as ortho- or para-phenylenediamines, ortho- or para-aminophenols, and heterocyclic compounds, which are generally referred to as oxidation bases. These oxidation bases, are colorless or weakly colored compounds which, when combined with oxidizing products, can give rise to colored compounds by a process of oxidative condensation.

It is also known that the shades obtained with these oxidation bases can be varied by combining them with couplers or coloration modifiers, the latter being chosen, for example, from meta-diaminobenzenes, meta-aminophenols, meta-diphenols, and certain heterocyclic compounds such as indole compounds.

The variety of molecules used as oxidation bases and couplers makes it possible to obtain a wide range of colors.

It is desirable for the "permanent" coloration obtained by means of these oxidation dyes to satisfy a certain number of requirements. For example, such a coloration typically may have at least one of the following properties: no toxicological drawbacks, allows shades of the desired intensity to be obtained, and shows good resistance to external agents such as light, bad weather, washing, permanent waving, perspiration and rubbing.

Other properties that may be possessed by such dyes include: allowing white hairs to be covered and being as unselective as possible, i.e., allowing the smallest possible differences in coloration to be produced over the entire length of the same keratin fiber, which may be differently sensitized (i.e. damaged) between its end and its root.

SUMMARY OF THE INVENTION

The present disclosure is directed to a novel family of N-alkylheteroaryl secondary para-phenylenediamines, which in one embodiment are capable of giving strong, aesthetic and sparingly selective colorations in varied shades, which may show good resistance to the various attacking factors to which the fibers may be subjected. The present disclosure also relates to a process for preparing these secondary para-phenylenediamines and also to their use in the oxidation dyeing of the hair.

An aspect of the disclosure is novel compositions for dyeing keratin fibers, for example, human keratin fibers such as the hair, comprising at least one N-alkylheteroaryl secondary para-phenylenediamine.

The composition of the present disclosure makes it possible to obtain a very strong and sparingly selective coloration of keratin fibers, which is fast, for example, with respect to light, while at the same time avoiding the degradation of these fibers. In addition, these compositions may have a good toxicological profile.

In one embodiment, the present disclosure is directed to a dyeing process using this composition for the dyeing of keratin fibers, for example, human keratin fibers such as the hair and also a kit comprising at least two compartments.

Other characteristics, aspects, subjects and advantages of the present disclosure will emerge even more clearly on reading the description and the examples that follow.

In the context of the present disclosure, the term "alkyl" means a linear or branched $C_1$-$C_{15}$ radical, for example, methyl, ethyl, n-propyl, isopropyl, butyl, etc. In addition, an alkoxy radical is a radical alk-O, the alkyl radical having the definition given above, for example methyloxy or ethyloxy. As used herein, the term "halogen" means Cl, Br, I or F.

BRIEF DESCRIPTION OF THE INVENTION.

The novel N-alkylheteroaryl secondary para-phenylenediamines according to the present disclosure are compounds of formula (I) and the addition salts thereof:

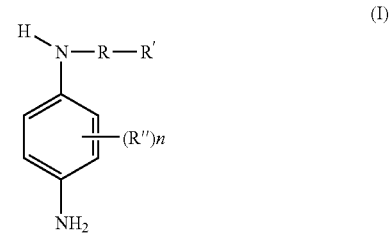

wherein:

R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl and dialkylaminocarbonyl group; the alkylene radical may be interrupted with at least one hetero atom chosen from oxygen and nitrogen or may be interrupted with at least one carbonyl function, R' is a heteroaryl group chosen from pyrrole, thiophene, pyrazole, triazole, oxazole, isoxazole, thiazole, isothiazole, pyridine, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals, R" is chosen from a hydrogen atom, an alkyl, alkoxy, hydroxyalkoxy, alkoxyalkyl, monohydroxyalkyl and polyhydroxyalkyl radical, and a halogen atom, n is an integer ranging from 1 to 4, with the proviso that the compound of formula (I) does not represent N-[2-(2-pyridyl)ethyl]-paraphenylenediamine.

For example, R is a linear or branched $C_2$-$C_4$ alkylene radical. Further for example, R comprises a hetero atom chosen from oxygen and nitrogen.

In one embodiment, R' is chosen from pyridine, pyrazole, and thiophene group.

Mention may be made to compounds of formula (I), for example:

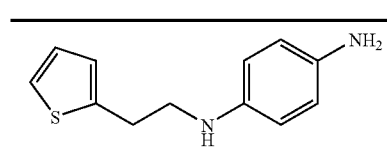
N-(2-Thiophen-2-yl)-ethylbenzene-1,4-diamine

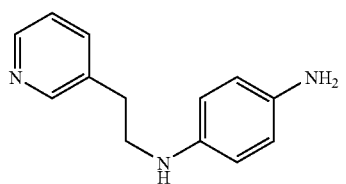
N-(2-Pyrid-3-ylethylbenzene-1,4-diamine

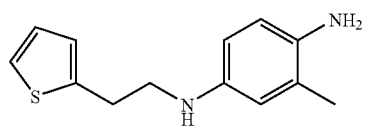
2-Methyl-N-4-(2-thiophen-2-yl-ethyl)benzene-1,4-diamine

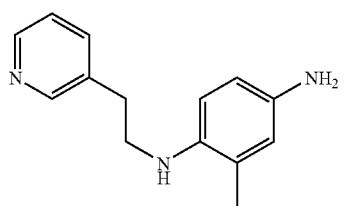
2-Methyl-N-1-(2-pyrid-3-yl-ethyl)benzene-1,4-diamine

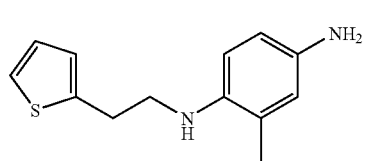
2-Methyl-N-1-(2-thiopen-2-yl-ethyl)benzene-1,4-diamine

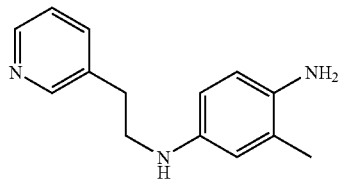
3-Methyl-N-1-(2-pyrid-3-ylethyl)benzene-1,4-diamine.

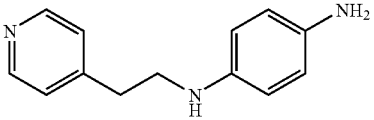
N-4-(2-pyrid-4-yl-ethyl)benzene-1,4-diamine

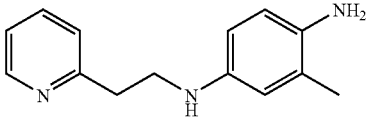
2-Methyl-N-4-(2-pyrid-2-yl-ethyl)benzene-1,4-diamine

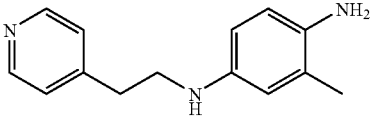
2-Methyl-N-4-(2-pyrid-4-yl-ethyl)benzene-1,4-diamine

-continued

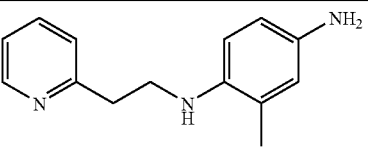
3-Methyl-N-4-(2-pyrid-2-yl-ethyl)benzene-1,4-diamine

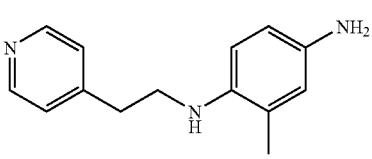
3-Methyl-N-4-(2-pyrid-4-ylethyl)-benzene-1,4-diamine

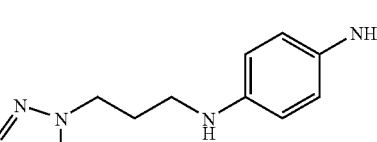
N-(3-Pyrazol-1-yl-propyl)benzene-1,4-diamine

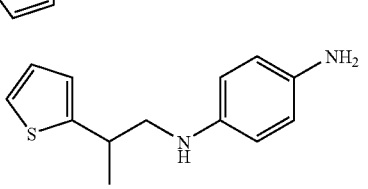
N-(2-Thiophen-2-yl-propyl)benzene-1,4-diamine

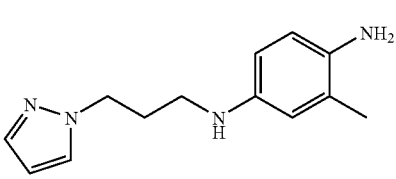
2-Methyl-N-4-(3-pyrazol-1-yl-propyl)benzene-1,4-diamine

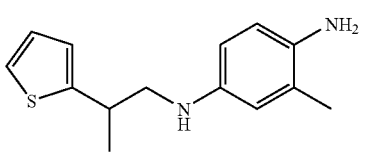
2-methyl-N-(2-Thiophen-2-yl-propyl)benzene-1,4-diamine

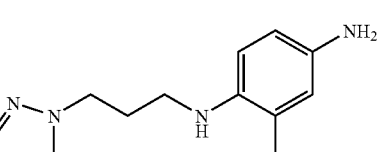
3-Methyl-N-4-(3-pyrazol-1-yl-propyl)benzene-1,4-diamine

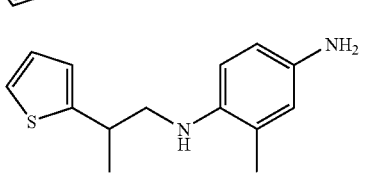
3-methyl-N-(2-Thiophen-2-yl-propyl)benzene-1,4-diamine

In general, the addition salts of the oxidation bases and couplers that may be used in the context of the disclosure are chosen, for example, from the addition salts with an acid, such as the hydrochlorides, hydrobromides, sulfates, citrates, succinates, tartrates, lactates, tosylates, benzenesulfonates, phosphates, and acetates.

The compounds of formula (I) according to the present disclosure may be prepared in general according to a process comprising the following steps:
nucleophilic substitution of the halogen in the para position in the para-halonitrobenzene derivative with a primary amine of formula R'RNH$_2$ in the presence of a base (R and R' being as defined above), and reduction of the nitro function of the compound obtained in the preceding step into an amine function, to obtain the compound of formula (I).

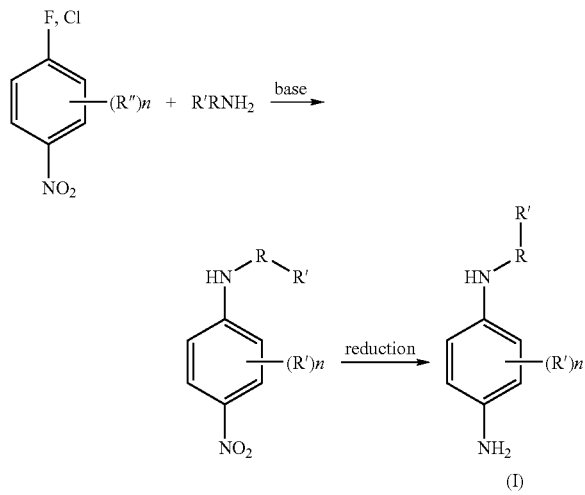

The first step of the synthesis is described in the reviews Synthesis 1990 (12), 1147-1148 and Synth. Commun. 1990, 20 (22), 3537-3545. The second step is a standard reduction step, for example, by performing a hydrogenation reaction via heterogeneous catalysis in the presence of Pd/C, Pd(II)/C or Raney Ni, or alternatively by performing a reduction reaction with a metal, for example with zinc, iron, tin, etc. (Advanced Organic Chemistry, 4$^{th}$ edition, 1992, J. March, Wiley Interscience; Reduction in Organic Chemistry, M. Hudlicky, 1983, Ellis Honwood series Chemical Science).

The present disclosure also is directed to the nitro compounds of formula (II) and processes for preparing the secondary para-phenylenediamine compounds of formula (I), wherein the step of reduction of the corresponding nitro compound of formula (II) is performed.

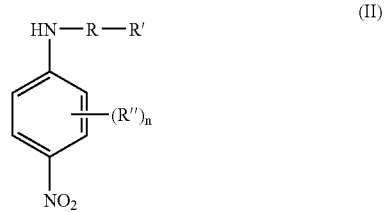

The present disclosure also relates to the compound of formula (I) and the addition salts thereof for the oxidation dyeing of the hair:

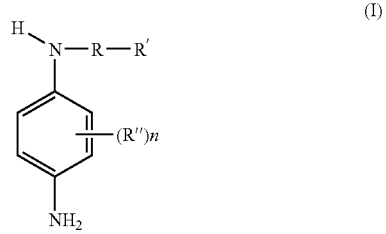

wherein:

R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group; the alkylene radical may be interrupted with at least one hetero atom chosen from oxygen and nitrogen or may be interrupted with at least one carbonyl function, R' is a heteroaryl group chosen from pyrrole, thiophene, pyrazole, triazole, oxazole, isoxazole, thiazole, isothiazole, pyridine, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals, R" is an entity chosen from a hydrogen atom, an alkyl, alkoxy, hydroxyalkoxy, alkoxyalkyl, monohydroxyalkyl and polyhydroxyalkyl radical, and a halogen atom, n is an integer ranging from 1 to 4.

The present disclosure also relates to a cosmetic composition for dyeing fibers, for example, keratin fibers such as the hair, comprising, in a cosmetically acceptable medium that is suitable for dyeing, at least one compound of formula (I) and the addition salts thereof:

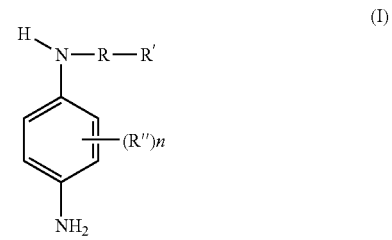

wherein:

R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group; the alkylene radical may be interrupted with at least one hetero atom chosen from oxygen and nitrogen or may be interrupted with at least one carbonyl function, R' is a heteroaryl group chosen from pyrrole, thiophene, pyrazole, triazole, oxazole, isoxazole, thiazole, isothiazole, pyridine, pyrimidine, pyrazine, triazine, and pyridazine groups, wherein the hetearyl group is unsubstituted or substituted with at least one radical chosen from alkyl, hydroxyl, alkoxy, sulfonamide, alkylcarbonyl amino, monoalkylamino, and dialkylamino radicals, R" is an entity chosen from a hydrogen atom, an alkyl, alkoxy, hydroxyalkoxy, alkoxyalkyl, monohydroxyalkyl and polyhydroxyalkyl radical, and a halogen atom, n is an integer ranging from 1 to 4.

For example, R is chosen from a linear and branched $C_2$-$C_4$ alkylene radical. Further for example, R is a hetero atom chosen from oxygen and nitrogen.

In one embodiment, R' is chosen from pyridine, pyrazole, and thiophene groups.

Compounds of formula (I) that may be mentioned, for example, are chosen from:

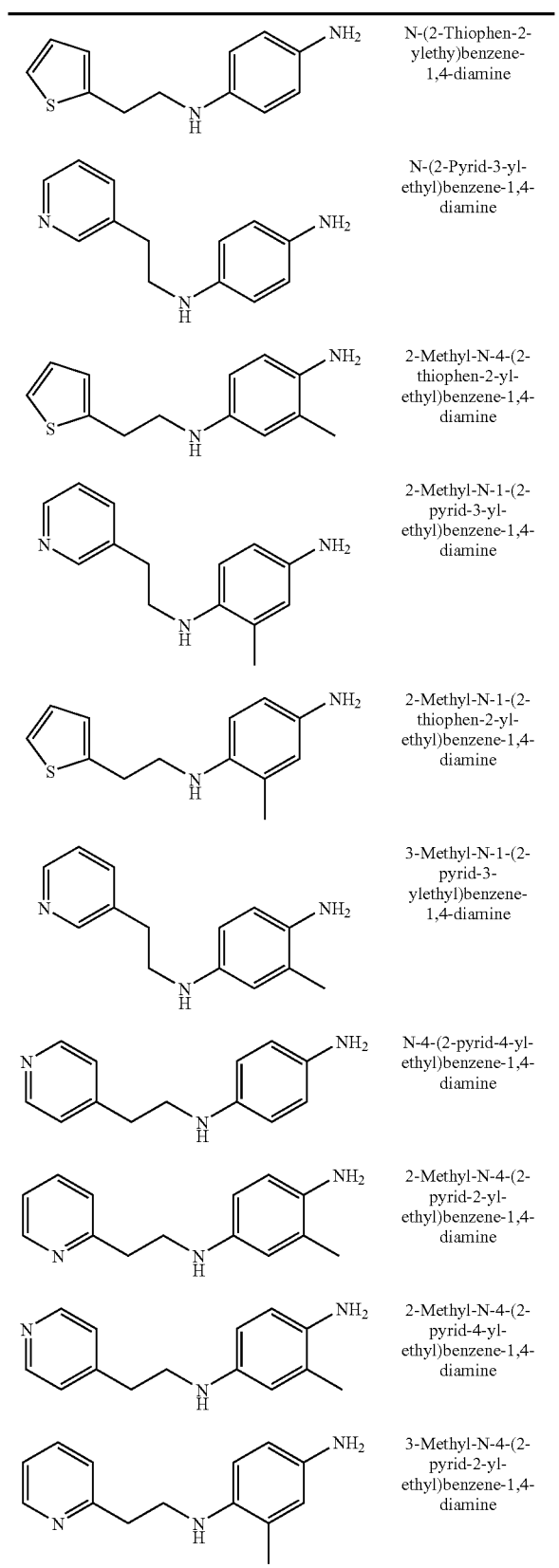
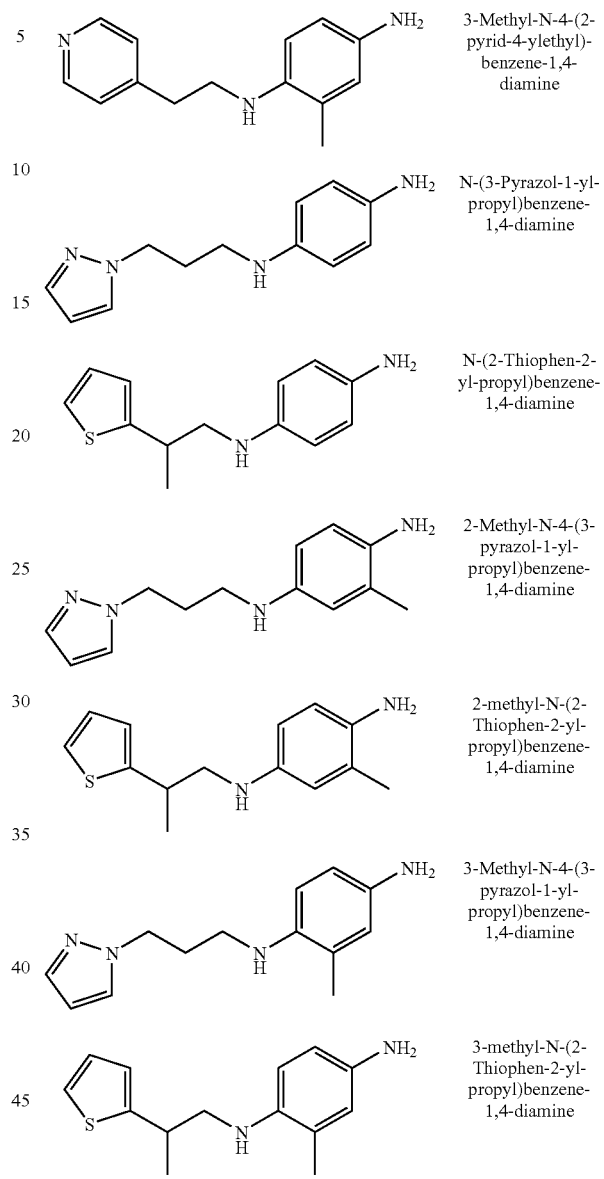

In one embodiment, the compound of formula (I) is present in an amount ranging from 0.0001% to 20% and for example, from 0.005% to 6%, by weight relative to the total weight of the composition.

The cosmetically acceptable medium that is suitable for dyeing is chosen from water and a mixture of water and of at least one organic solvent, for example, branched and unbranched $C_1$-$C_4$ lower alcohols, such as ethanol and isopropanol; polyols and polyol ethers, for example, 2-butoxyethanol, propylene glycol, propylene glycol monomethyl ether, diethylene glycol monomethyl ether and monoethyl ether; glycerol and also aromatic alcohols, for example, benzyl alcohol and phenoxyethanol; and mixtures thereof.

The at least one organic solvent is, for example, present in an amount ranging from 1% to 40%, by weight approximately and further for example, from 5% to 30%, by weight approximately relative to the total weight of the dye composition.

The cosmetic composition in accordance with the disclosure further comprises at least one cosmetic adjuvant chosen from the group formed by antioxidants, penetrating agents, sequestering agents, fragrances, buffers, dispersants, surfactants, conditioning agents, film-forming agents, polymers, ceramides, preserving agents, nacreous agents and opacifiers, and vitamins and provitamins.

The at least one adjuvant is generally present in an amount for each of them ranging from 0.01% to 20%, by weight relative to the weight of the composition.

The composition of the present disclosure, for example, further comprises at least one oxidation coupler. Among the at least one oxidation coupler that may be mentioned, for example, are meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

Generally, the at least one oxidation coupler is present in an amount ranging from 0.0001% to 20%, and for example, from 0.005% to 6%, by weight relative to the total weight of the composition.

The composition of the present disclosure further comprises at least one additional oxidation dye precursor other than the compounds of formula (I).

The at least one additional oxidation base may be chosen, for example, from para-phenylenediamines, bis(phenyl)alkylenediamines, para-aminophenols, ortho-amino phenols, heterocyclic bases, and the addition salts thereof.

Among the para-phenylenediamines, mention may be made, for example, to para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidone, 6-(4-aminophenylamino)hexan-1-ol, and the addition salts thereof with an acid.

In one embodiment, the para-phenylenediamines mentioned above are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamines, 2-β-acetylaminoethyloxy-para-phenylenediamines, and the addition salts thereof with an acid.

Among the bis(phenyl)alkylenediamines, mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof with an acid.

Among the para-aminophenols, mention may be made, by way of example, of para-aminophenol, 4-amino-2-methylphenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis(5'-amino-2'-hydroxy)phenylmethane, and the addition salts thereof with an acid.

Among the ortho-aminophenols, mention may be made, for example, of 2-aminophenol, 2-amino-5-methylphenol, 2-amino-6-methylphenol, 5-acetamido-2-amino-phenol, and the addition salts thereof with an acid.

Among the heterocyclic bases, mention may be made, for example, of pyridine derivatives, pyrimidine derivatives, and pyrazole derivatives.

Among the pyridine derivatives, mention may be made of the compounds described, for example, in United Kingdom Patent Nos. GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases that are useful in the present disclosure are, for example, 3-aminopyrazolo[1,5-a]pyridine oxidation bases or the addition salts thereof described, for example, in French Patent Application No. FR 2 801 308. Examples that may be mentioned include pyrazolo[1,5-a]pyrid-3-ylamine; 2-acetylaminopyrazolo-[1,5-a]pyrid-3-ylamine; 2-morpholin-4-ylpyrazolo[1,5-a]pyrid-3-ylamine; 3-aminopyrazolo-[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyridine-6-ol; 3-aminopyrazolo[1,5-a]pyrid-7-ol; and also the addition salts thereof with an acid.

Among the pyrimidine derivatives, mention may be made of the compounds described, for example, in German Patent No. DE 2 359 399; Japanese Patent Nos. JP 88-169 571 and JP 05 63 124; European Patent No. EP 0 770 375, and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives, mention may be made of the compounds described in German Patent Nos. DE 3 843 892 and DE 4 133 957, International Patent Application Nos. WO 94/08969 and WO 94/08970, French Patent No. FR-A-2,733,749, and German Patent No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

Generally, the at least one oxidation base is present in an amount ranging from 0.0001% to 20% and for example, from 0.005% to 6%, by weight relative to the total weight of the composition.

In general, the addition salts of the oxidation bases and couplers that may be used in the context of the disclosure are chosen, for example, from the addition salts with an acid such as the hydrochlorides, hydrobromides, sulfates, citrates, succinates, tartrates, lactates, tosylates, benzenesulfonates, phosphates, and acetates.

The dye composition in accordance with the disclosure may further comprise at least one direct dye, which may be chosen from neutral, acidic and cationic nitrobenzene dyes; neutral, acidic and cationic azo direct dyes; neutral, acidic and cationic quinine; and for example, anthraquinone direct dyes, azine direct dyes, triarylmethane direct dyes, indoamine direct dyes, and natural direct dyes. In one embodiment, the composition according to the disclosure comprises at least one dye chosen from cationic direct dyes and natural direct dyes.

Among the cationic direct dyes that may be used according to the disclosure, mention may be made of the cationic azo direct dyes described in International Patent Application Nos. WO 95/15144 and WO 95/01772, and European Patent No. EP 714 954.

Among these compounds, mention may be made, for example, of the following dyes:

1,3-dimethyl-2-[[4-(dimethylamino)phenyl]azo]-1H-imidazolium chloride;

1,3-dimethyl-2-[(4-aminophenyl)azo]-1H-imidazolium chloride; and 1-methyl-4-[(methylphenylhydrazono)methyl]pyridinium methyl sulfate.

Among the natural direct dyes that may be used according to the disclosure, mention may be made, for example, of lawsone, juglone, alizarin, purpurin, carminic acid, kermesic acid, purpurogallin, protocatechaldehyde, indigo, isatin, curcumin, spinulosin, and apigenidin. Extracts or decoctions comprising these natural dyes and for example, henna-based poultices or extracts may be used.

The at least one direct dye is present in an amount ranging from 0.001% to 20% by weight approximately, and for example, from 0.005% to 10% by weight approximately, relative to the total weight of the ready-to-use composition.

A ready-to-use dye composition is obtained by adding at least one oxidizing agent. The at least one oxidizing agent conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for example, laccases. In one embodiment, hydrogen peroxide is the at least one oxidizing agent.

Needless to say, a person skilled in the art will take care to select this or these optional additional compound(s) such that the advantageous properties intrinsically associated with the oxidation dye composition in accordance with the disclosure are not, or are not substantially, adversely affected by the envisaged addition(s).

The pH of the dye composition in accordance with the disclosure ranges from 3 to 12 approximately, and for example, from 5 to 11 approximately. The pH value may be adjusted to the desired value using acidifying or basifying agents usually used in the dyeing of keratin fibers, or alternatively using standard buffer systems.

Among the acidifying agents that may be mentioned, for example, are mineral or organic acids other than carboxylic diacids, such as hydrochloric acid, orthophosphoric acid, sulfuric acid, carboxylic acids, for example, acetic acid, tartaric acid, citric acid and lactic acid, and sulfonic acids.

Among the basifying agents that may be mentioned, for example, are aqueous ammonia, alkali metal carbonates, alkanolamines such as monoethanolamine, diethanolamine and triethanolamine and also derivatives thereof, sodium hydroxide, potassium hydroxide and the compounds of formula:

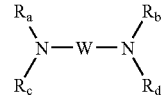

wherein W is a propylene residue optionally substituted with an entity chosen from a hydroxyl group and a $C_1$-$C_4$ alkyl radical; $R_a$, $R_b$, $R_c$ and $R_d$, which may be identical or different, are chosen from hydrogen atoms and $C_1$-$C_4$ alkyl and $C_1$-$C_4$ hydroxyalkyl radicals.

The dye composition according to the disclosure may be in various forms, such as in the form of liquids, creams or gels, or in any other form that is suitable for dyeing keratin fibers, such as human hair.

In one embodiment, the present disclosure relates to a process wherein the composition according to the present disclosure as defined above is applied to the fibers and the color is developed using at least one oxidizing agent. The color may be developed at acidic, neutral or alkaline pH. The at least one oxidizing agent may be added to the composition of the disclosure just at the time of use. It may be used starting with an oxidizing composition containing it, which is applied simultaneously or sequentially to the composition of the disclosure.

According to one embodiment, the composition according to the present disclosure is mixed, such as at the time of use, with a composition comprising, in a cosmetically acceptable medium that is suitable for dyeing, at least one oxidizing agent, the at least one oxidizing agent is present in an amount that is sufficient to develop a coloration. The mixture obtained is then applied to the keratin fibers. After an action time ranging from 3 to 50 minutes approximately and for example, 5 to 30 minutes approximately, the keratin fibers are rinsed, washed with shampoo, rinsed again and then dried.

The oxidizing composition may also comprise at least one adjuvant conventionally used in hair dye compositions and as defined above.

The pH of the oxidizing composition comprising the at least oxidizing agent is such that, after mixing with the dye composition, the pH of the resulting composition applied to the keratin fibers, for example, ranges from 3 to 12 approximately such as from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, such as human hair.

The present disclosure also relates to the use of the cosmetic composition according to the disclosure comprising, in a cosmetically acceptable medium that is suitable for dyeing, at least one compound of general formula (I) for dyeing fibers, for example, keratin fibers such as the hair.

In one embodiment, the present disclosure is directed to a kit comprising at least two compartments, wherein a first compartment comprises the dye composition defined above and a second compartment comprises an oxidizing composition. The kit may be equipped with a device for applying the desired mixture to the hair, such as the devices described in French Patent No. FR-2 586 913.

Using this device, it may be possible to dye keratin fibers via a process that includes mixing a dye composition in accordance with the disclosure with at least one oxidizing agent as defined above, and applying the mixture obtained to the keratin fibers for a time that is sufficient to develop the desired coloration.

Other than in the operation examples, or where otherwise indicated, all numbers expressing quantities of ingredients, reaction conditions, and so forth used in the present specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that numerical ranges and parameters setting forth the broad scope of the disclosure are approximations, the numerical values set forth in the specific examples are reported to as precisely as possible. Any numerical value, however, inherently contains certain error necessarily resulting from the standard deviation found in their respective testing measurements.

The examples that follow serve to illustrate the disclosure without, however, being limiting in nature.

EXAMPLES

Example 1

Synthesis of N-(2-thiophen-2-ylethyl)benzene-1,4-diamine dihydro-chloride (2)

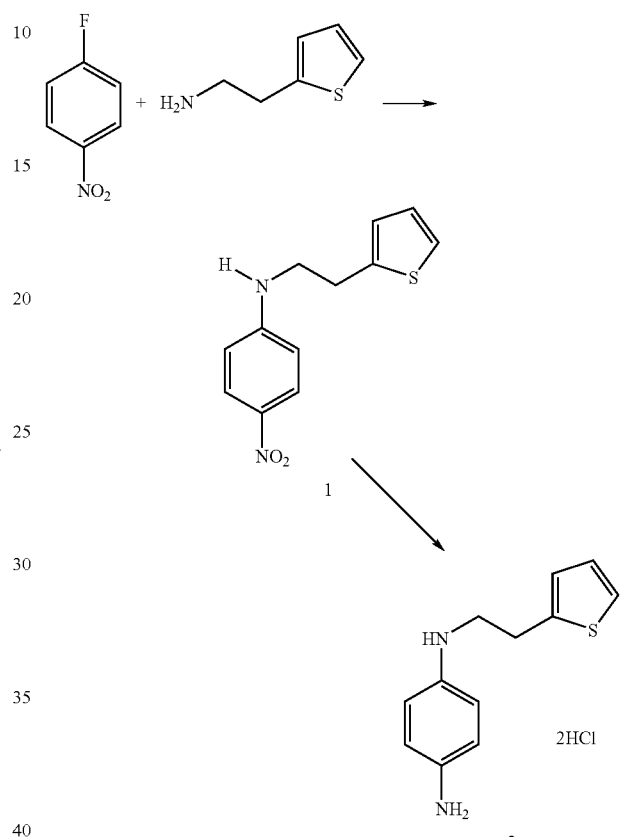

Step 1

Synthesis of N-(4-nitrophenyl)-N-(2-thien-2-ylethyl) amine 2 g of 4-fluoronitrobenzene, 2.16 g of 2-thien-2-ylethanamine, and 2.35 g of $K_2CO_3$ were added to a solution of 20 ml of N-methyl-pyrrolidinone. The reaction medium was heated at 60° C. for 12 hours and, after cooling to room temperature, was then poured into a water+ice mixture. The yellow precipitate formed was filtered off, reslurried in water and then dried over $P_2O_5$. 3.3 g of N-(4-nitrophenyl)-N-(2-thien-2-ylethyl)amine (1) were obtained.

Step 2

Synthesis of N-(2-thiophen-2-ylethyl)benzene-1,4-diamine dihydrochloride (2)

The N-(4-nitrophenyl)-N-(2-thien-2-ylethyl)amine (1) obtained above was reduced with a boiling zinc/ammonium chloride/water/ethanol mixture. The corresponding amine was isolated in dihydrochloride form.

The proton NMR and mass spectra were in accordance with the expected structure of the product.

Example 2

Synthesis of N-(2-pyrid-3-ylethyl)benzene-1,4-diamine (4)

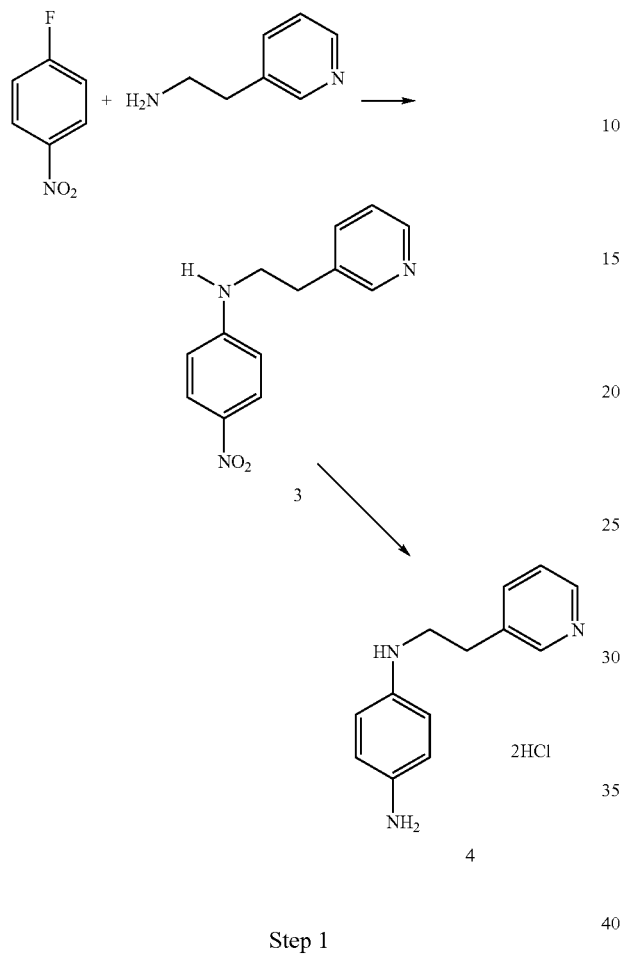

Step 1

Synthesis of N-(4-nitrophenyl)-N-(2-pyrid-3-ylethyl)amine (3)

2 g of 4-fluoronitrobenzene, 2.07 g of 2-(3-pyridyl)ethylamine, and 2.35 g of $K_2CO_3$ were added to a solution of 20 ml of N-methylpyrrolidinone. The reaction medium was heated at 60° C. for 16 hours and, after cooling to room temperature, was then poured into a water+ice mixture. The yellow precipitate formed was filtered off, reslurried in water, and then dried over $P_2O_5$. 3.2 g of N-(4-nitrophenyl)-N-(2-pyrid-3-ylethyl)amine (3) were obtained.

Step 2

Synthesis of N-(2-pyrid-3-ylethyl)benzene-1,4-diamine (4)

The N-(4-nitrophenyl)-N-(2-pyrid-3-ylethyl)amine (3) obtained above was reduced with a boiling zinc/ammonium chloride/water/ethanol mixture. The corresponding amine was isolated in dihydrochloride form.

The proton NMR and mass spectra were in accordance with the expected structure of the product.

Application to locks of hair of a composition obtained from mixing, before application, a standard dye support comprising the compound obtained above with an oxidizing composition, made it possible to obtain colored locks.

Example 3

Synthesis of N-(2-pyrid-2-ylethyl)benzene-1,4-diamine dihydrochloride (6)

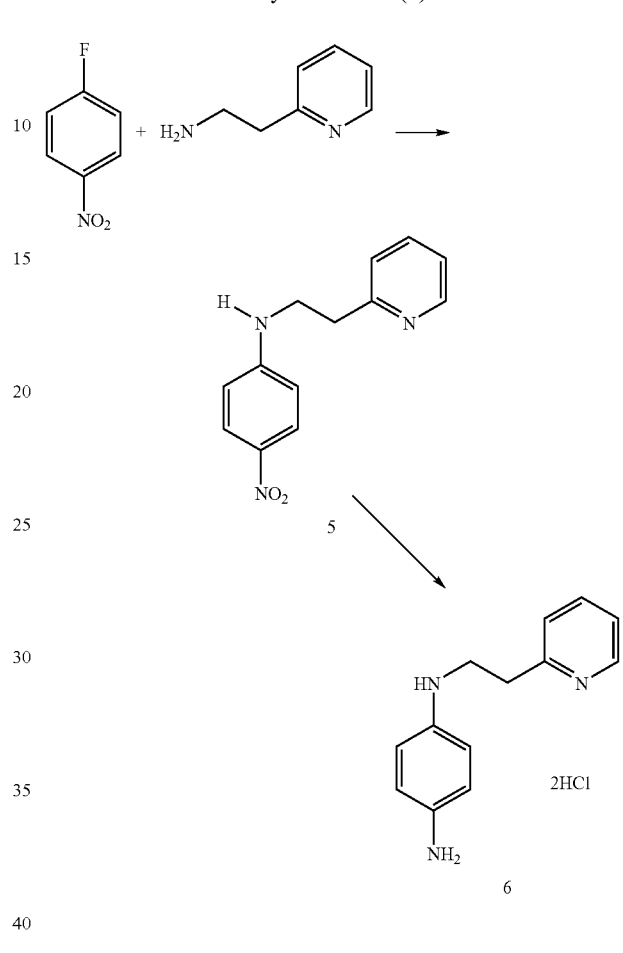

Step 1

Synthesis of N-(4-nitrophenyl)-N-(2-pyrid-2-ylethyl)amine (5)

2 g of 4-fluoronitrobenzene, 2.07 g of 2-(2-aminoethyl)pyridine, and 2.35 g of $K_2CO_3$ were added to a solution of 20 ml of N-methylpyrrolidinone. The reaction medium was heated at 60° C. for 18 hours and, after cooling to room temperature, was then poured into a water+ice mixture. The yellow precipitate formed was filtered off, reslurried in water and then dried over $P_2O_5$. 3.3 g of N-(4-nitrophenyl)-N-(2-pyrid-2-ylethyl)amine (5) were obtained.

Step 2

Synthesis of N-(2-pyrid-2-ylethyl)benzene-1,4-diamine dihydrochloride (6)

The N-(4-nitrophenyl)-N-(2-pyrid-2-ylethyl)amine (5) obtained above was reduced with a boiling zinc/ammonium chloride/water/ethanol mixture. The corresponding amine was isolated in dihydrochloride form.

The proton NMR and mass spectra were in accordance with the expected structure of the product.

Example 4

Synthesis of 2-methyl-N-1-(2-pyrid-2-ylethyl)benzene-1,4-diamine dihydrochloride (8)

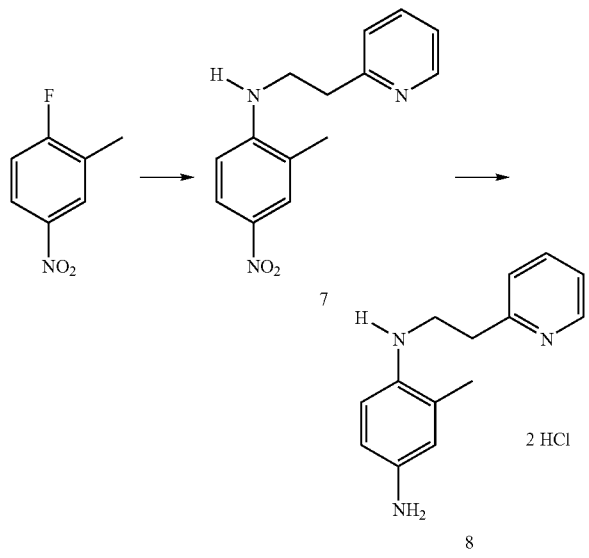

Step 1

Preparation of N-(2-methyl-4-nitrophenyl)-N-(2-pyrid-2-ylethyl)amine (7)

3.1 g (0.02 mol) of 2-fluoro-5-nitrotoluene, 2.65 g (0.025 mol) of sodium carbonate, and 5 ml of NMP (N-methylpyrrolidone) were introduced into a three-necked flask under nitrogen. 2.37 g (0.022 mol) of 2-(2-aminoethyl)pyridine in 10 ml of NMP (N-methylpyrrolidone) were added dropwise with stirring. The mixture was heated to 90° C. After reaction for 56 hours, the reaction mixture was cooled and 50 ml of distilled water were then added slowly with vigorous stirring. A yellow precipitate formed. This precipitate was filtered off, washed several times with water and then with pentane, and dried under vacuum. 5 g of expected nitro derivative were obtained in the form of a yellow powder.

Step 2

Preparation of 2-methyl-N-1-(2-pyrid-2-ylethyl)benzene-1,4-diamine dihydrochloride (8)

2 g of nitro derivative (7) prepared above and about 80 ml of methanol were introduced into a 200 ml autoclave (hydrogenator) equipped with a magnetic stirrer. The solution obtained was degassed with nitrogen. 0.3 g of palladium-on-charcoal (5% humidity, containing 50% water) was added thereto. The reaction mixture was stirred, while flushing once with hydrogen, and hydrogen was then introduced to a pressure of about 5 bar. After reaction for 4 hours, the reactor was flushed with nitrogen and the reaction medium was filtered quickly through Celite and under a gentle pressure of nitrogen. The filtrate was recovered into a precooled solution of methanol containing about 3 equivalents of hydrogen chloride gas. The filter cake was rinsed several times with methanol under a stream of nitrogen. The solution thus obtained was concentrated and was then treated with ether. The product obtained, in the form of a pale pink paste, was stirred and then rinsed several times with acetonitrile and with ether under nitrogen. 2 g of expected product (8) were isolated in the form of a slightly pink white powder.

The proton NMR and $^{13}$C spectra and microanalyses were in accordance with the expected structure of the product.

Example 5

Synthesis of N-(4-amino-2-methoxyphenyl)-N-(2-pyrid-2-ylethyl)amine dihydrochloride (10)

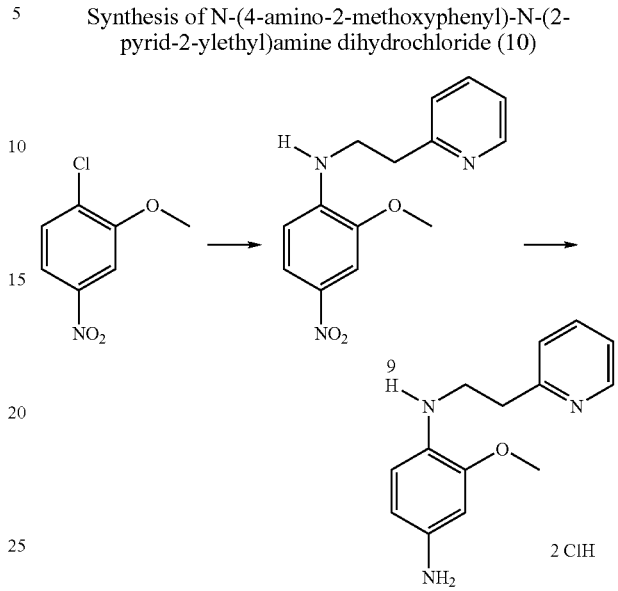

Step 1

Preparation of N-(2-methoxy-4-nitrophenyl)-N-(2-pyrid-2-ylethyl)amine (9)

5.62 g (0.03 mol) of 2-chloro-5-nitroanisole, 4 g (0.038 mol) of sodium carbonate, 4.5 g (0.037 mol) of 2-(2-ethylamino)pyridine, and 25 ml of NMP were introduced into a three-necked flask under nitrogen. The mixture was heated to 10° C. After reaction for 6 days, the reaction mixture was cooled and 75 ml of distilled water were then added slowly with vigorous stirring. The nitro derivative appeared in the form of a brown semi-solid, and was extracted with dichloromethane and then purified on a column of silica, eluting with 2/3 ethyl acetate/heptane. 2.1 g of expected nitro derivative (9) were obtained in the form of an orange solid. The proton NMR and $^{13}$C spectra and microanalyses were in accordance with the expected structure of the product.

Step 2

Preparation of N-(4-amino-2-methoxyphenyl)-N-(2-pyrid-2-yl-ethyl)amine dihydrochloride (10)

The N-(2-methoxy-4-nitrophenyl)-N-(2-pyrid-2-ylethyl)amine (9) obtained above was reduced with a boiling zinc/ammonium chloride/water/ethanol mixture. The corresponding amine was isolated in dihydrochloride form.

The proton NMR and mass spectra were in accordance with the expected structure of the product.

Examples of Dyeing

Examples 1 to 14

Dye Composition Using N-(2-pyrid-3-ylethyl)benzene-1,4-diamine (4)

Examples 1 to 7

Dyeing in Acidic Medium

The following dye compositions were prepared:

|  | Example | | | | | | |
| --- | --- | --- | --- | --- | --- | --- | --- |
|  | 1 | 2 | 3 | 4 | 5 | 6 | 7 |
| N-(2-Pyrid-3-ylethyl)benzene-1,4-diamine (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
| --- | --- |
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

A.M. = Active material.

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | | | | | | |
| --- | --- | --- | --- | --- | --- | --- | --- |
|  | 1 | 2 | 3 | 4 | 5 | 6 | 7 |
| Shade observed | strong grey | strong violet | strong brown | strong red-grey | strong brown | strong blue | strong violet |

Examples 8 to 14

Dyeing in Basic Medium

The following dye compositions were prepared:

|  | Example | | | | | | |
| --- | --- | --- | --- | --- | --- | --- | --- |
|  | 8 | 9 | 10 | 11 | 12 | 13 | 14 |
| N-(2-Pyrid-3-ylethyl)benzene-1,4-diamine (4) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |

-continued

|  | Example | | | | | | |
|---|---|---|---|---|---|---|---|
|  | 8 | 9 | 10 | 11 | 12 | 13 | 14 |
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

A.M. = Active material.

At the time of use, each composition was mixed with an equal weight of 20-volumes aqueous hydrogen peroxide solution (6% by weight). A final pH of 9.5 was obtained.

Examples 15 to 28

Dye Composition using
N-(2-pyrid-2-ylethyl)benzene-1,4-diamine
dihydrochloride (6)

Examples 15 to 21

Dyeing in Acidic Medium

The following dye compositions were prepared:

|  | Example | | | | | | |
|---|---|---|---|---|---|---|---|
|  | 15 | 16 | 17 | 18 | 19 | 20 | 21 |
| N-(2-Pyrid-2-ylethyl)benzene-1,4-diamine dihydrochloride (6) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | | | | | | |
|---|---|---|---|---|---|---|---|
|  | 8 | 9 | 10 | 11 | 12 | 13 | 14 |
| Shade observed | brown | strong violet | orange | red-brown | red | strong blue | strong blue-violet |

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

A.M. = Active material.

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | | | | | | |
| --- | --- | --- | --- | --- | --- | --- | --- |
|  | 15 | 16 | 17 | 18 | 19 | 20 | 21 |
| Shade observed | strong brown | strong violet-grey | strong brown | strong red-brown | red-brown | strong blue-grey | strong blue-violet |

Examples 22 to 28

Dyeing in Basic Medium

The following dye compositions were prepared:

|  | Example | | | | | | |
| --- | --- | --- | --- | --- | --- | --- | --- |
|  | 22 | 23 | 24 | 25 | 26 | 27 | 28 |
| N-(2-Pyrid-2-ylethyl)-benzene-1,4-diamine dihydrochloride (6) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo[5,1-c]-[1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| 96° ethyl alcohol | 20.8 g |
| --- | --- |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

A.M. = Active material.

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | | | | | | |
| --- | --- | --- | --- | --- | --- | --- | --- |
|  | 22 | 23 | 24 | 25 | 26 | 27 | 28 |
| Shade observed | orange-brown | strong violet | orange | red-brown | strong red | strong blue | strong blue-violet |

Examples 29 to 42

Dye Composition using N-(2-thiophen-2-ylethyl)benzene-1,4-diamine dihydrochloride (2)

Examples 29 to 35

Dyeing in Acidic Medium

The following dye compositions were prepared:

| | Example | | | | | | |
|---|---|---|---|---|---|---|---|
| | 29 | 30 | 31 | 32 | 33 | 34 | 35 |
| N-(2-Thiophen-2-ylethyl)benzene-1,4-diamine dihydrochloride (2) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

A.M. = Active material.

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

| | Example | | | | | | |
|---|---|---|---|---|---|---|---|
| | 29 | 30 | 31 | 32 | 33 | 34 | 35 |
| Shade observed | strong brown | strong violet-grey | strong grey | strong brown | strong red-brown | strong blue-violet | strong violet-grey |

Examples 36 to 42

Dyeing in Basic Medium

The following dye compositions were prepared:

|  | Example | | | | | | |
|---|---|---|---|---|---|---|---|
|  | 36 | 37 | 38 | 39 | 40 | 41 | 42 |
| N-(2-Thiophen-2-yl-ethyl)benzene-1,4-diamine dihydrochloride (2) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyrid-3-ol | | | | $10^{-3}$ mol | | | |
| 3,6-Dimethyl-1H-pyrazolo-[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

A.M. = Active material.

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The shades obtained were given in the table below:

|  | Example | | | | | | |
|---|---|---|---|---|---|---|---|
|  | 36 | 37 | 38 | 39 | 40 | 41 | 42 |
| Shade observed | orange-brown | strong violet | strong red | strong red-brown | strong red | strong blue-violet | strong blue-violet |

What is claimed is:

1. A compound of formula (I) and the addition salts thereof:

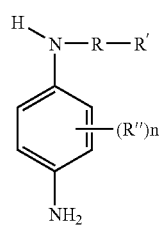

(I)

wherein:

R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group, and where the alkylene radical is optionally interrupted with at least one entity chosen from a heteroatom chosen from oxygen and nitrogen and a carbonyl;

R' is a heteroaryl group chosen from pyrrole, thiophene, pyrazole, triazole, oxazole, isoxazole, thiazole, isothiazole, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;

R'' is an entity chosen from a hydrogen atom, an alkyl, alkoxy, hydroxyalkoxy, alkoxyalkyl, monohydroxyalkyl and polyhydroxyalkyl radical, and a halogen atom;

n is an integer ranging from 1 to 4; and with the proviso that the compound of formula (I) does not represent N-[2-(2-pyridyl)ethyl]-para-phenylenediamine.

2. The compound according to claim 1, wherein R is the $C_2$-$C_{10}$ alkylene radical interrupted with at least one entity chosen from a heteroatom chosen from oxygen and nitrogen and a carbonyl.

3. The compound according to claim 2, wherein the heteroatom is chosen from oxygen and nitrogen.

4. The compound according to claim 1, wherein R is chosen from a linear and branched $C_2$-$C_4$ alkylene radical.

5. The compound according to claim 1, wherein R' is chosen from pyrazole, and thiophene groups.

6. The compound according to claim 1 chosen from:
N-(2-Thiophen-2-ylethyl)benzene-1,4-diamine;
2-Methyl-N-4-(2-thiophen-2-ylethyl)benzene-1,4-diamine;
2-Methyl-N-1-(2-thiophen-2-ylethyl)benzene-1,4-diamine;
N-(3-Pyrazol-1-ylpropyl)benzene-1,4-diamine;
N-(2-Thiophen-2-ylpropyl)benzene-1,4-diamine;
2-Methyl-N-4-(3-pyrazol-1-ylpropyl)benzene-1,4-diamine;
2-Methyl-N-(2-thiophen-2-ylpropyl)benzene-1,4-diamine;
3-Methyl-N-4-(3-pyrazol-1-ylpropyl)benzene-1,4-diamine;
3-Methyl-N-(2-thiophen-2-ylpropyl)benzene-1,4-diamine; and the addition salts thereof.

7. The compound according to claim 1, wherein the addition salts of formula (I) are chosen from the hydrochlorides, hydrobromides, sulfates, citrates, succinates, tartrates, lactates, tosylates, benzenesulfonates, phosphates, and acetates.

8. A nitro compound of formula (II) and the addition salts thereof:

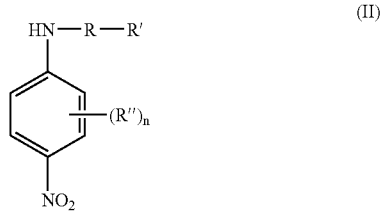

(II)

wherein:
R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group, and wherein the alkylene radical is optionally interrupted with at least one entity chosen from a heteroatom chosen from oxygen and nitrogen and a carbonyl;
R' is a heteroaryl group chosen from pyrrole, thiophene, pyrazole, triazole, oxazole, isoxazole, thiazole, isothiazole, pyrimidine, pyrazine, triazine and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;
R'' is an entity chosen form a hydrogen atom, an alkyl, alkoxy, hydroxyalkoxy, alkoxyalkyl, monohydroxyalkyl and polyhydroxyalkyl radical, and a halogen atom; and
n is an integer ranging from 1 to 4.

9. The compound according to claim 8, wherein R is the alkylene radical interrupted with at least one entity chosen from a heteroatom chosen from oxygen and nitrogen and a carbonyl.

10. A process for preparing a compound of formula (I) and the addition salts thereof:

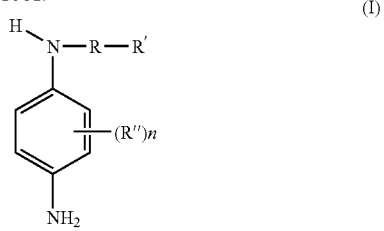

(I)

wherein:
R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group and wherein the alkylene radical is optionally interrupted with at least one entity chosen from a heteroatom chosen from oxygen and nitrogen and a carbonyl;
R' is a heteroaryl group chosen from pyrrole, thiophene, pyrazole, triazole, oxazole, isoxazole, thiazole, isothiazole, pyrimidine, pyrazine, triazine and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radical;
R'' is an entity chosen from a hydrogen atom, an alkyl, alkoxy, hydroxyalkoxy, alkoxyalkyl, monohydroxyalkyl and polyhydroxyalkyl radicals, and a halogen atom; and
n is an integer ranging from 1 to 4,
comprising reducing a nitro compound of formula (II) and the addition salts thereof:

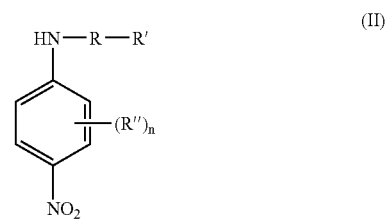

(II)

wherein:
R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group and wherein the alkylene radical is optionally interrupted with at least one entity chosen from a heteroatom chosen from oxygen and nitrogen and a carbonyl;
R' is a heteroaryl group chosen from pyrrole, thiophene, pyrazole, triazole, oxazole, isoxazole, thiazole, isothiazole, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;
R'' is an entity chosen from a hydrogen atom, an alkyl, alkoxy, hydroxyalkoxy, alkoxyalkyl, monohydroxyalkyl and polyhydroxyalkyl radical, and a halogen atom; and
n is an integer ranging from 1 to 4.

11. A composition for dyeing keratin fibers comprising, in a cosmetically acceptable medium, at least one compound of formula (I) and the addition salts thereof:

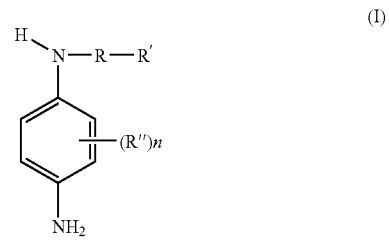

(I)

wherein:
R is a linear $C_2$-$C_{10}$ alkylene radical, wherein the alkylene radical is unsubstituted or substituted radical with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group and wherein the alkylene radical is optionally interrupted with at least one entity chosen from a heteroatom chosen from oxygen and nitrogen and a carbonyl;

R' is a heteroaryl group chosen from pyrrole thiophene, pyrazole, triazole, oxazole, isoxazole, thiazole, isothiazole, pyridine, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino and dialkylamino radicals;

R" is chosen from a hydrogen atom, an alkyl, alkoxy, hydroxyalkoxy, alkoxyalkyl, monohydroxyalkyl and polyhydroxyalkyl radical, and a halogen atom; and n is an integer ranging from 1 to 4.

12. The composition according to claim 11, wherein R is the alkylene radical interrupted with at least one entity chosen from a heteroatom chosen from oxygen and nitrogen and a carbonyl.

13. The composition according to claim 11, wherein R is chosen from a linear and branched $C_2$-$C_4$ alkylene radical.

14. The composition according to claim 11, wherein R' is chosen from a pyridine, pyrazole, and thiophene groups optionally bearing a substituent chosen from —CH$_3$, —CH$_2$CH$_3$, —OCH$_3$, —OH, and —SO$_2$NH$_2$.

15. The composition according to claim 11, wherein the compound of formula (I) is chosen from:
N-(2-Thiophen-2-ylethyl)benzene-1,4-diamine;
N-(2-Pyrid-3-ylethyl)benzene-1,4-diamine;
2-Methyl-N-4-(2-thiophen-2-ylethyl)benzene-1,4-diamine;
2-Methyl-N-1-(2-pyrid-3-ylethyl)benzene-1,4-diamine;
2-Methyl-N-1-(2-thiophen-2-ylethyl)benzene-1,4-diamine;
3-Methyl-N-1-(2-pyrid-3-ylethyl)benzene-1,4-diamine;
N-4-(2-Pyrid-4-ylethyl)benzene-1,4-diamine;
2-Methyl-N-4-(2-pyrid-2-ylethyl)benzene-1,4-diamine;
2-Methyl-N-4-(2-pyrid-4-ylethyl)benzene-1,4-diamine;
3-Methyl-N-4-(2-pyrid-2-ylethyl)benzene-1,4-diamine;
3-Methyl-N-4-(2-pyrid-4-ylethyl)benzene-1,4-diamine;
N-(3-Pyrazol-1-ylpropyl)benzene-1,4-diamine;
N-(2-Thiophen-2-ylpropyl)benzene-1,4-diamine;
2-Methyl-N-4-(3-pyrazol-1-ylpropyl)benzene-1,4-diamine;
2-Methyl-N-(2-thiophen-2-ylpropyl)benzene-1,4-diamine;
3-Methyl-N-4-(3-pyrazol-1-ylpropyl)benzene-1,4-diamine;
3-Methyl-N-(2-thiophen-2-ylpropyl)benzene-1,4-diamine; and
the addition salts thereof.

16. The composition according to claim 11, wherein the addition salts with an acid of the compounds of formula (I) are chosen from the hydrochlorides, hydrobromides, sulfates, citrates, succinates, tartrates, lactates, tosylates, benzenesulfonates, phosphates, and acetates.

17. The composition according to claim 11, wherein the compound of formula (I) is present in an amount ranging from 0.0001% to 20%, by weight relative to the total weight of the composition.

18. The composition according to claim 11, wherein the cosmetically acceptable medium is chosen from water and a mixture of water and of at least one organic solvent chosen from branched and unbranched $C_1$-$C_4$ lower alcohols, polyols and polyol ethers, aromatic alcohols, and mixtures thereof.

19. The composition according to claim 11, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents and opacifiers, and vitamins and provitamins.

20. The composition according to claim 19, wherein the at least one cosmetic adjuvant is present in an amount ranging from 0.01% to 20%, by weight relative to the total weight of the composition.

21. The composition according to claim 11, further comprising at least one coupler chosen from meta-phenylenediamines, meta-aminophenols, meta-diphenols, naphthalene-based couplers, and heterocyclic couplers.

22. The composition according to claim 21, wherein the at least one coupler is present in an amount ranging from 0.0001% to 20%, by weight relative to the total weight of the composition.

23. The composition according to claim 11, further comprising at least one additional oxidation base other than the compound of formula (I), chosen from para-phenylenediamines, bis(phenyl)alkylenediamines, para-aminophenols, ortho-aminophenols and heterocyclic bases, and the addition salts thereof.

24. The composition according to claim 23, wherein the at least one additional oxidation base is present in an amount ranging from 0.0001% to 20%, by weight relative to the total weight of the composition.

25. The composition according to claim 11, further comprising at least one direct dye chosen from cationic and natural direct dyes.

26. A process for dyeing keratin fibers comprising applying to the fibers, for a time that is sufficient to develop a desired coloration in the presence of an oxidizing agent, a cosmetic composition comprising, in a cosmetically acceptable medium, at least one compound of formula (I) and the addition salts thereof:

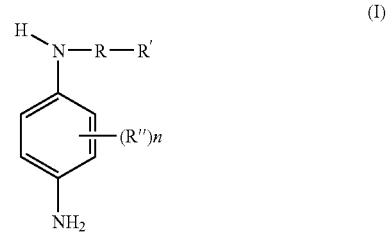

wherein:
R is a linear $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl, and dialkylaminocarbonyl group and wherein the alkylene radical is optionally interrupted with at least one entity chosen from a heteroatom chosen from oxygen and nitrogen and a carbonyl;

R' is a heteroaryl group chosen from pyrrole, thiophene, pyrazole, triazole, oxazole, isoxazole, thiazole, isothiazole, pyridine, pyrimidine, pyrazine, triazine and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;

R" is an entity chosen from a hydrogen atom, an alkyl, alkoxy, hydroxyalkoxy, alkoxyalkyl, monohydroxyalkyl and polyhydroxyalkyl radical, and a halogen atom;

n is an integer ranging from 1 to 4.

27. A ready-to-use composition comprising a cosmetic composition comprising, in a cosmetically acceptable medium, at least one compound of formula (I) and the addition salts thereof:

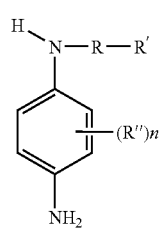

wherein:

R is a $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl and dialkylaminocarbonyl group and wherein the alkylene radical is optionally interrupted with at least one entity chosen from a heteroatom chosen from oxygen and nitrogen and a carbonyl;

R' is a heteroaryl group chosen from pyrrole, thiophene, pyrazole, triazole, oxazole, isoxazole, thiazole, isothiazole, pyridine, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;

R" is an entity chosen from a hydrogen atom, an alkyl, alkoxy, hydroxyalkoxy, alkoxyalkyl, monohydroxyalkyl and polyhydroxyalkyl radical, and a halogen atom;

n is an integer ranging from 1 to 4; and at least one oxidizing agent chosen from hydrogen peroxide, urea peroxide, alkali metal bromates, persalts, peracids, and oxidase enzymes.

28. A kit comprising at least two compartments, wherein the first compartment comprises a dye composition for dyeing keratin fibers comprising at least one compound of formula (I) and the addition salts thereof:

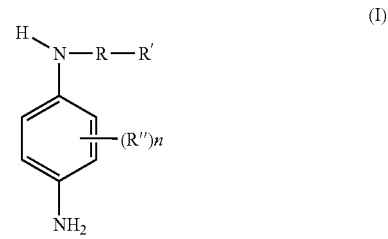

wherein:

R is a linear $C_2$-$C_{10}$ alkylene radical, wherein the alkylene radical is unsubstituted or substituted with at least one group chosen from a halogen atom and an alkyl, alkoxy, amino, hydroxyl, monoalkylamino, dialkylamino, alkylcarbonyl, carboxyl, amido, alkoxycarbonyl, monoalkylaminocarbonyl and dialkylaminocarbonyl group and wherein the alkylene radical is optionally interrupted with at least one entity chosen from a heteroatom chosen from oxygen and nitrogen and a carbonyl;

R' is a heteroaryl group chosen from pyrrole, thiophene, pyrazole, triazole, oxazole, isoxazole, thiazole, isothiazole, pyridine, pyrimidine, pyrazine, triazine, and pyridazine groups, wherein the heteroaryl group is unsubstituted or substituted with at least one radical chosen from alkyl, hydroxyl, alkoxy, sulfonamide, alkylcarbonyl amino, monoalkylamino, and dialkylamino radicals;

R" is an entity chosen from a hydrogen atom, an alkyl, alkoxy, hydroxyalkoxy, alkoxyalkyl, monohydroxyalkyl and polyhydroxyalkyl radical, and a halogen atom; and n is an integer ranging from 1 to 4, and the second compartment comprising at least one oxidizing agent.

* * * * *